US006422746B1

(12) United States Patent
Weiss et al.

(10) Patent No.: US 6,422,746 B1
(45) Date of Patent: Jul. 23, 2002

(54) METHOD AND DEVICE FOR A SELF ORIENTING FLOATING APPARATUS

(75) Inventors: Ferdinand Weiss, New Milford; Robert Grieble, Lackawanna, both of PA (US)

(73) Assignee: G & W Instruments, Inc., Carbondale, PA (US)

( * ) Notice: Subject to any disclaimer, the term of this patent is extended or adjusted under 35 U.S.C. 154(b) by 0 days.

(21) Appl. No.: 09/447,917

(22) Filed: Nov. 23, 1999

(51) Int. Cl.$^7$ .............................. G01K 1/14; G01D 5/12; G01D 7/02; B63B 22/00; B63B 22/24; G01N 9/14
(52) U.S. Cl. ..................... 374/156; 374/142; 374/194; 374/208; 116/204; 116/216; 441/32; 441/21; 73/448; 73/866.3
(58) Field of Search ................... 374/156, 208, 374/194, 142; 73/32 R, 866.3, 448, 449, 453, 451; 116/204, 208, 216; 114/144 E; 441/32, 21

(56) References Cited

U.S. PATENT DOCUMENTS

| 2,040,292 A | * | 5/1936 | Brown ...................... 374/156 |
| 2,635,461 A | | 4/1953 | Groth et al. |
| 2,809,525 A | * | 10/1957 | Savage ...................... 374/156 |
| 3,442,142 A | | 5/1969 | Gresham |
| 3,475,975 A | | 11/1969 | Sokol et al. |
| 3,871,108 A | * | 3/1975 | Beaudout ...................... 33/349 |
| 3,888,201 A | * | 6/1975 | Zuvela ...................... 114/144 R |
| 3,952,761 A | * | 4/1976 | Friedland ...................... 73/452 |
| 3,956,831 A | * | 5/1976 | Sibley ...................... 33/362 |
| 3,961,531 A | * | 6/1976 | Peng ...................... 73/353 |
| 3,964,317 A | | 6/1976 | Blanchard ...................... 73/453 |
| 4,400,978 A | | 8/1983 | Guay et al. ...................... 73/453 |
| 4,731,036 A | * | 3/1988 | Ulf ...................... 441/2 |
| 5,013,161 A | * | 5/1991 | Zaragoza et al. ........... 374/208 |
| 5,045,836 A | * | 9/1991 | Nobles, Jr. ...................... 340/450 |
| 5,848,029 A | | 12/1998 | Chang ...................... 368/229 |
| 5,893,789 A | | 4/1999 | Wu ...................... 446/129 |
| 5,900,547 A | * | 5/1999 | Bartkiewicz ...................... 73/447 |

FOREIGN PATENT DOCUMENTS

| JP | 61095228 | * | 5/1986 | ................ 73/32 R |
| JP | 63047630 | * | 2/1988 | ................ 73/32 R |

* cited by examiner

Primary Examiner—Diego Gutierrez
Assistant Examiner—Gail Verbitsky
(74) Attorney, Agent, or Firm—McNees Wallace & Nurick LLC; Mitchell A. Smolow; Carmen Santa Maria

(57) ABSTRACT

The present invention relates to a method and device for a self orienting floating apparatus which utilizes an external magnetic field to maintain a constant orientation, and specifically relates to a plain form hydrometer, a floating thermometer, and a thermohydrometer that continuously display a graduated scale in an operator pre-determined direction.

24 Claims, 2 Drawing Sheets

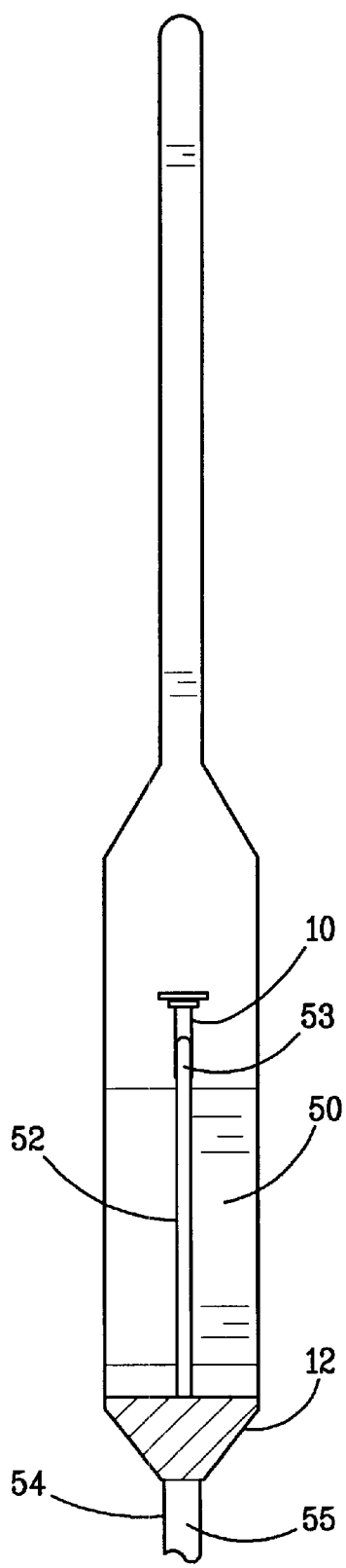 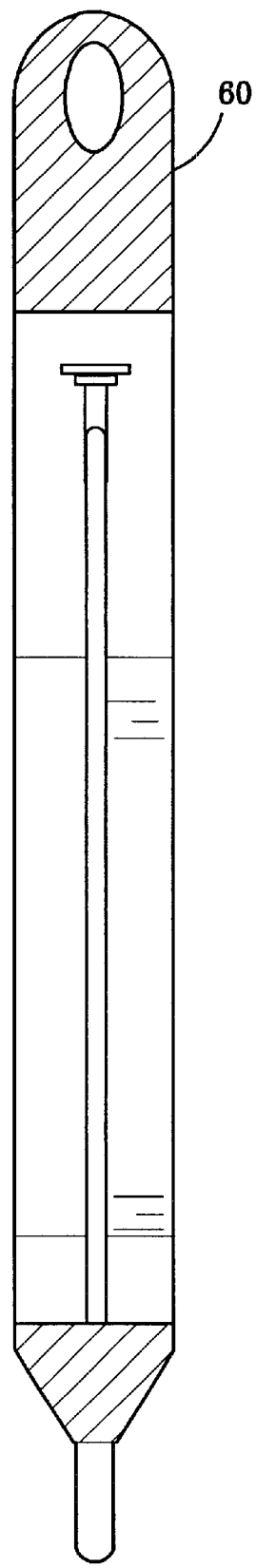
FIG. 4                    FIG. 5

METHOD AND DEVICE FOR A SELF ORIENTING FLOATING APPARATUS

BACKGROUND OF THE INVENTION

1. Field of the Invention

The present invention relates to a method and device for self orienting a floating apparatus which utilizes an external magnetic field to maintain a constant orientation, and specifically relates to a plain form hydrometer, a floating thermometer, and a thermohydrometer that continuously display a graduated scale in an operator predetermined direction.

2. Discussion of the Related Art

Various instruments have been used by both industry and the home owner to measure properties such as the density, (weight per unit volume) specific gravity (weight per unit volume compared with water), or temperature of various liquids. Examples are floating thermometers, used to measure temperature, hydrometers used to measure density, and thermohydrometers which are a combination of a floating thermometer and a constant mass, variable displacement type hydrometer ("plain form hydrometer"). Plain form hydrometers and thermohydrometers ("plain form instruments") have been made of either glass or plastic. These instruments typically comprise a body having a lower ballast section having a weight secured within this section for weighting of the instrument, and a stem portion that is integrally formed with the ballast. The stem contains a rolled scale that is numbered to correspond to the liquid being tested, and provide for a direct read-out of the desired measurement. Different scales have been utilized for different applications. For example, in determining specific gravity, the following scales have been used: Baume, API (petroleum), Proof and Tralle (alcohol), Brix (sugar), salt, and percentage scales. Fahrenheit, Celsius, and Kelvin temperature scales have also been utilized.

These instruments are used by placing them in the liquid in which a desired measurement is to be obtained. In the case of a hydrometer, an appropriate density of the liquid can be read from the scale contained within the stem of the device, determined by the amount the hydrometer extends into the liquid. Likewise, the temperature can be read from the face of the scale contained within a thermohydrometer or floating thermometer. Such floating hydrometers have been described, for example, in U.S. Pat. No. 4,993,263.

When instruments are floating in a liquid, they have a tendency to spin in circles, causing the scale to face away from the user. The user invariably has to gently touch the instrument or stretch his/her neck in order to read the scale.

Magnetic fields have been utilized to control the position of floating objects. U.S. Pat. No. 4,400,978 to Guay, et al, discloses an electronic hydrometer having an electronic circuit capable of automatically controlling the position of a float by means of a variable current supply and providing an output signal indicative of the density of a liquid. A permanent magnet is mounted in proximity of a connecting shaft which is secured to a float which is disposed within a liquid receiving chamber. The magnet is utilized in conjunction with an electronic circuit to maintain a plate mounted on the shaft in a reference position relative to a beam of light, and not to orient the scale to a predetermined position.

U.S. Pat. No. 3,964,317 to Blanchard discloses a densimeter which utilizes a float to sense a density of a fluid. Through the use of (1) an electric current, (2) a cylindrical coil connected to the end of a shaft which is connected to a float, and (3) a permanent magnet, the float is maintained at a selected vertical reference position. In the invention of the '317 patent, the magnet does not orient the scale to a predetermined rotational position.

U.S. Pat. No. 5,848,029 to Chang and U.S. Pat. No. 5,893,789 to Wu utilize magnetic forces to control the movement of a floating toy. These toys are not used to provide a readout, are not used for measuring, and do not need to be positioned in a fixed direction relative to the user. Magnetic forces are used to provide random movement to the toy.

What is needed is a method and device to be used on a floating apparatus that will allow a readout to orient in a position such that the readout is continuously facing a predetermined direction.

Use of the term "related art" is descriptive in nature only and references cited are not admitted to be "prior art" with respect to the present invention by their mention in this Background Section. All references cited are incorporated by reference as if fully set forth herein.

SUMMARY OF THE INVENTION

The present invention relates to a device for self orienting a readout integral to a floating apparatus utilizing a magnet integral to a container. For purposes of this invention, integral means positioned within, affixed to a wall, affixed within, engraved or etched or printed on a wall or otherwise located within or on the apparatus. The container may be of any size or shape having sufficient volume to float. The magnet and/or the readout can be embedded in a cylinder, attached externally to a cylinder, integral with a cylinder, or placed within a cylinder, being supported by the apparatus or supported by an additional structure within the apparatus.

One structure which accomplishes this comprises attaching an orienting magnet to a pin, the pin having a first and a second end. The orienting magnet is attached to the first end (pinhead) of the pin. The second end of the pin is affixed to the apparatus by a first means to allow the orienting magnet to resistively rotate. A second means is provided to rotate the orienting magnet to a predetermined position such that when the orienting magnet is aligned with an external magnetic field, the readout of the apparatus orients itself in a direction pre-selected by a user, the pre-selected direction being independent of the external magnetic field.

The present invention also relates to a method for directionally orienting a readout of a floating apparatus which comprises the steps of:

a) integrating an orienting magnet to the floating apparatus, b) orienting the magnet to a position relative to an external magnetic field, such that when the magnet aligns with the external magnetic field, a readout fixed to the floating apparatus orients itself to face a preselected direction. In one embodiment, the orienting magnet is integrated by resistively rotatably attaching.

The term "resistively rotatably attaching" means, for the purpose of this invention, the ability to rotate the orienting magnet only upon utilizing a force greater than the attractive forces between the orienting magnet and the apparatus, as explained in greater detail below.

A second embodiment comprises a device and method in which the orienting magnet is attached to the first end of the pin in a predetermined position. The second end of the pin is affixed to the apparatus so as to not allow the first permanent magnet to rotate, such that when the orienting magnet is aligned with an external magnetic field, the readout of the apparatus orients itself in a direction pre-selected by a user, the pre-selected direction being independent of the external magnetic field.

A third embodiment comprises embedding an orienting magnet within or on the apparatus such that when the orienting magnet is aligned with an external magnetic field, the readout of the apparatus orients itself in a direction pre-selected by a user, the pre-selected direction being independent of the external magnetic field.

Still another embodiment comprises either permanently or resistively rotatably affixing an orienting magnet to the readout and allowing the readout to float in a liquid contained within the apparatus such that when the orienting magnet is aligned with an external magnetic field, the readout of the apparatus orients itself in a direction pre-selected by a user, the pre-selected direction being independent of the external magnetic field.

In particular, an advantage of the present invention is to provide a device and method such that a plain form hydrometer, a floating thermometer, a thermohydrometer, or other floating instrument can be inexpensively and conveniently preset to face a predetermined direction.

Other features and advantages of the present invention will be apparent from the following more detailed description of the preferred embodiment, taken in conjunction with the accompanying drawings which illustrate, by way of example, the principles of the invention.

BRIEF DESCRIPTION OF THE DRAWINGS

For the purpose of illustrating the invention, there is shown in the drawings forms which are presently preferred; it being understood, however, that the invention is not limited to the precise arrangement and instrumentalities shown.

FIG. 4 is a representative drawing of a thermohydrometer with the directional device of the present invention.

FIG. 5 is a representative drawing of a floating thermometer with the directional device of the present invention.

DETAILED DESCRIPTION OF THE INVENTION

Figures 1, 2, 3:
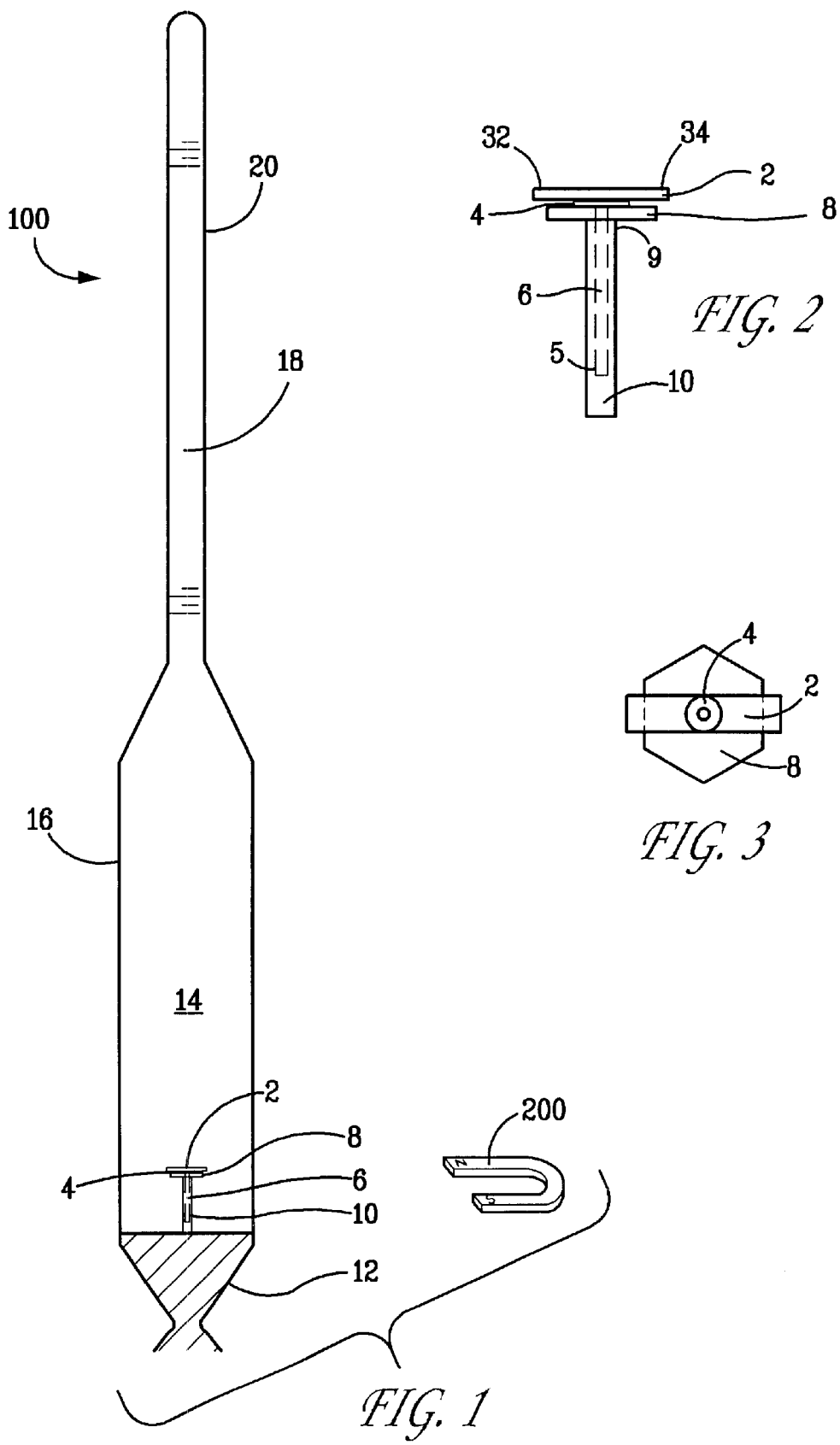
FIG. 1 is a representative drawing of a plain form hydrometer with the directional device of the present invention.
FIG. 2 is a representative drawing of a side view of the magnet, nut, pin and tube assembly.
FIG. 3 is a representative drawing of a top view of the magnet, nut, pin and tube assembly.

Referring now to the drawings in detail, where, whenever possible, like numerals refer to like parts or elements, there is shown in FIG. 1 the present invention of the device for an orienting floating plain form hydrometer 100 which utilizes a magnetic field to maintain a constant orientation.

The preferred embodiment of the present invention, as shown in FIG. 1 through FIG. 3, comprises an orienting magnet 2 attached to the head 4 of a pin 6 which passes through a nut 8 into a tube 10 which is anchored in ballast 12. The ballast 12 is contained within the body 14 of a cylinder 16 containing a readout 18.

The hydrometer 100 of the preferred embodiment comprises a cylinder 16, generally made of glass or plastic, that is wide on the lower end and narrower at the top. This wider lower end is called the body 14 and the narrower top end is called the stem 20. Contained within the lowest end of the body 14 is the ballast 12 which makes the hydrometer sink in a particular liquid (not shown). By placing the ballast 12 in the lowest end of the body 14, the center of gravity of the cylinder 16 is located in a manner so as to cause the cylinder 16 to float upright with the ballast 12 submerged when placed in a liquid (not shown). Generally, as is typically in the prior art, the ballast 12 comprises a material of sufficient density to locate the center of gravity of the cylinder 16 in a manner as described above. The ballast 12 may be, by way of example, lead, steel, grains of silica, or other heavy materials dense enough to displace the center of gravity of the cylinder 16 sufficiently downward so as to give the cylinder 16 stability when floating upright in a liquid. A preferred ballast is linotype, which is an alloy of antimony, lead and tin.

The ballast 12 is initially in a form that will allow insertion of the tube 10 into the ballast 12. The ballast 12 is, for example, ball shaped, powder, or granular in form. The ballast 12 may be located in place, for example by melting the ballast into a solid mass, by utilizing melted and then cooled wax, by applying an adhesive, or any of the other methods known to those skilled in the art. An appropriate amount of ballast 12 is inserted into the body 14 and located in place so as to properly calibrate the hydrometer.

Contained within the stem 20 is a readout. The readout is, for example, a rolled scale 18 that is numbered to correspond to the liquid being tested. Such a scale may be, for example, a Baume scale, an API scale, a Proof and Tralle scale, a Brix scale, a salt scale, or a percentage scale. Fahrenheit, Celsius, and Kelvin temperature scales as well as any other scale utilized to measure a property of a liquid may also be used. Alternatively, the readout is an electronic readout. The scale 18 is made of, for example, paper, plastic, or metal and secured by, for example, an adhesive such as Permabond manufactured by Permabond Corp., Division of National Starch and Chemical or other appropriate adhesive, or mechanically fixed, such as by crimping a metal tie, or frictionally held in place. The scale may also be scribed, etched or painted onto the interior or exterior of the stem 20.

A tube 10 is positioned vertically in the center of the ballast 12 such that the orienting magnet 2 is able to align itself with an external magnetic field (not shown). The tube 10 may be manufactured of, for example, glass, plastic, or metal such as, for example, stainless steel. The second end 11 of the tube 10 is anchored in the ballast 12 by, for example, placing the tube 10 in molten ballast 12 and allowing the ballast 12 to solidify around the tube 10. By way of example, the second end 11 of the tube 10 is inserted in ballast 12 comprising a plurality of linotype balls. Linotype balls comprise a mixture of antimony, lead and tin. The body 14 is held upright by placement into sand of appropriate depth to support the body 14. The sand is then heated by methods known to those skilled in the art to a temperature sufficient to melt the ballast 12, but not the body 14. Alternatively, the ballast 12 comprises a mixture of material as described above and wax. After insertion of the second end 11 of the tube 10 into the ballast 12 wax mixture, the mixture is heated and cooled by known methods sufficient for the wax to melt and re-solidify around the tube 10 and ballast 12 so as to create a single mass able to maintain the tube 10 in the desired position.

The tube 10 extends above the surface of the ballast 12 a sufficient distance to support a pin 6. This distance is about 29 mm and the tube 10 diameter is about 3 mm i.d. However, it should be appreciated that the tube dimensions, as well as all other dimensions of the present invention are dependant upon the shape of the body 14 and may be varied as required for a particular situation.

Permanently attached to a first, open end 9 of the tube 10 is a nut 8 made of steel, cobalt or other ferromagnetic material. The nut 8 is affixed by an adhesive bonding with an adhesive such as, for example, Permabond, or other appropriate adhesive, or mechanically fixed, such as, for example, by threading or by swaging. For purposes of this embodiment, swaging involves inserting a tool into the first end 9 of the tube 10 in such a manner as to expand the outside diameter of the first end 9 of the tube 10 against the inner walls of the nut opening (not shown) to provide the mechanical attachment of the nut 8 to the tube 10. The nut 8 is attached horizontally, so that the nut opening (not shown) aligns with the first, open end 9, allowing access to the interior of the tube 10.

The head of the pin 4 is larger in diameter than the nut opening (not shown), so that when the second end of the pin 5 is inserted into the first end 9 of the tube 10, the pin 6 is prevented from falling through the nut 8. Additionally, the pinhead 4 separates the orienting magnet 2 from the nut 8 allowing it to resistively rotate. This separation is the thickness of the pinhead 4, usually about 0.5 mm. The magnetic attraction between the orienting magnet 2 and the nut 8 resists any tendency for the orienting magnet 2 to rotate freely, thus keeping the orienting magnet 2 pointing in a preset direction relative to the scale 18 (FIG. 1).

As shown in FIGS. 2 and 3, the pin 6 has at its first end a pinhead 4. The pin 6 is manufactured of any material, and is typically steel or plastic. The pinhead 4 is about 4 mm in diameter, and the pin 6 is about 2 mm in diameter and about 20 mm in length. Permanently attached to the pinhead 4 is an orienting magnet 2. The orienting magnet 2 may be attached using an adhesive such as, for example, Permabond, or other appropriate adhesive, or it may be attached by an electro-mechanical means, such as, for example, by spot welding. The orienting magnet 2 is attached in a horizontal plane to the pinhead 4, perpendicular to the pin 6 axis, such that the North Pole 32 and the South Pole 34 of the orienting magnet 2 are 180 degrees opposed. The orienting magnet 2 is about 3 mm by about 10 mm.

In a preferred embodiment the orienting magnet 2 resistively rotates using a combination of a ferromagnetic nut 8 having a central opening, the tube 10 having the first open end 9 opposed to the second end 11, and the pin 6 having a head 4 on a first end, the head 4 larger in diameter than the tube central opening. The pinhead 4 is opposed to the pin second end 5, wherein the orienting magnet 2 is affixed to the pinhead 4; the tube second end 11 is affixed to the apparatus; the tube 10 extends upward; and the nut 8 is affixed to the tube first open end 9 and aligned to allow passage of the pin second end 11 until the pinhead 4 rests on the nut 8, so that a space remains between the orienting magnet 2 and the nut 8.

In use, the operator determines in what direction the readout 18 (in the preferred embodiment, a gravity scale), should orient. Utilizing the magnetic attraction between a handheld direction setting magnet 200, and the orienting magnet 2, the operator rotates the orienting magnet 2 to a position such that when the orienting magnet 2 aligns itself with an external magnetic field (not shown), the gravity scale 18 orients in the desired direction.

The magnetic attraction between the orienting magnet 2 and the handheld direction setting magnet 200 is stronger than the magnetic attraction between the orienting magnet 2 and the ferromagnetic nut 8, thus allowing movement of the hand held direction setting magnet to rotate the orienting magnet 2.

The magnetic attraction between the orienting magnet 2 and the nut 8 is greater than the frictional and surface tension forces between the outside walls of the cylinder 16 and the liquid (not shown) in which the cylinder 16 floats. Therefore, as the orienting magnet 2 aligns itself with the external magnetic force, it will remain in the same relative position to the nut 8 and the entire cylinder 16 will rotate within the liquid (not shown) so that the scale 18 will orient to the predetermined position.

In this way, once the orienting magnet 2 is properly set, the gravity scale 18 will continuously face the desired direction, rather than rotating as the cylinder 16 spins within the liquid as it would without the present invention.

The external magnetic field may be the earth's gravitational field, an electromagnetic field, or any other operator applied magnetic field.

FIG. 4 shows a second embodiment of a device for a self orienting floating instrument according to the present invention.

As seen in the thermohydrometer of FIG. 4, in the present embodiment, a thermometer scale 50 is positioned above and adjacent to the ballast 12. The barrel of the thermometer 52 has a first 53 and second 55 end, and is positioned vertically, such that the second end 55 terminates in a thermometer bulb 54 which extends beneath the ballast 12. The tube 10 is attached to the firs end 53 and is secured by, for example, an adhesive such as Permabond or other appropriate adhesive, or mechanically fixed, such as by crimping a metal tie, or frictionally held in place, to the first end of the thermometer barrel 52. In all other respects, the embodiment of FIG. 4 is the same as the preferred embodiment of FIG. 1 through FIG. 3. For the sake of clarity, the individual parts not directly connected with the invention have been omitted from FIG. 4.

The floating thermometer embodiment of FIG. 5 differs from that of FIG. 4 only in that the gravity scale 18 is not present, but rather the body 14 and stem 20 are equal in diameter, with the stem 20 culminating in a ring 60. Otherwise, the arrangement of FIG. 5 is identical with that of FIG. 4. For the sake of clarity, the individual parts not directly connected with the invention have been omitted from FIG. 5.

Most laboratories have a designated area where solutions are tested. The present invention would allow a laboratory to preset their instruments such that the gravity scale 18 would be continuously facing the technician, thus saving time and making it convenient for the technician to read the instrument. Optionally, rather than having the orienting magnet 2 be operator controlled, the orienting magnet 2 may be factory present in a desired position.

In yet another embodiment of the present invention, the orienting magnet 2 is factory set to a fixed permanent positioned. The tube 10 and nut 8 are omitted and the second end 5 of the pin 6 is non-rotatably affixed, using methods such as, for example, those described above for affixing the tube second end 11 to the ballast 12 of FIG. 1 or to the superior end of the thermometer barrel 52 of FIGS. 4 and 5.

Although the present invention has been described in considerable detail with reference to certain preferred versions thereof, other versions are possible. For example, the present invention may be used in what is commonly called "syringe type hydrometers".

In a syringe type hydrometer, the operator puts one end in a liquid and draws the liquid up in a glass or plastic cylinder using a rubber bulb. The instrument floats in the drawn solution to give a reading. The present invention can be utilized so that the floating instrument contained within the syringe type hydrometer continuously faces in a desired direction.

In yet another variation, the present invention may have the orienting magnet integral with the apparatus, such as, for example, embedded within the ballast, or attached to the apparatus, such as, for example, by using an adhesive to adhere the orienting magnet to the internal or external surfaces of the apparatus, or painting a magnetic material on a surface of the apparatus, and rotating the readout to a position such that the readout will orient itself to this preselected position upon alignment of the orienting magnet with an external magnetic field. This rotation of the readout may be accomplished, for example, by painting, etching, or scribing the readout to a rotating section of the cylinder, or by rotatably affixing a readout to the apparatus, either within or outside of the cylinder, such as, for example, by painting, etching, or scribing a readout on a sleeve fitting around or within the cylinder, or attaching a readout to a shaft affixed either within or without the cylinder.

In another variation, an orienting magnet may be either permanently or resistively rotatably attached (as previously described) to the readout. The cylinder is partially filled with a liquid having a density greater than the readout. The readout is placed within the cylinder so as to float in the liquid. When the orienting magnet orients itself to an external magnetic field, the floating readout will orient itself to the predetermined direction.

The present invention may also be used in a floating buoy so as to continually orient a sign affixed to the buoy in a preset direction.

Although the present invention has been described in connection with specific examples and embodiments, those skilled in the art will recognize that the present invention is capable of other variations and modifications within its scope. These examples and embodiments are intended as typical of, rather than in any way limiting on, the scope of the present invention as presented in the appended claims.

What is claimed is:

1. A self orienting floating apparatus comprising:
   a housing,
   a pin having a first and second end, said second pin end in a fixed relation to said housing;
   said orienting magnet attached to said first pin end, and
   a readout integral with said housing,
   such that when said orienting magnet is aligned with an external magnetic field,
   said readout orients itself in a direction pre-selected by a user, the pre-selected direction being independent of the external magnetic field.

2. The apparatus of claim 1 wherein the housing is a cylinder.

3. The apparatus of claim 1 wherein the readout is indicative of at least one floating apparatus determined physical property selected from the group consisting of specific gravity, temperature and density.

4. The apparatus of claim 1 wherein the readout is a rolled scale.

5. The apparatus of claim 1 wherein the readout is an electronic readout.

6. The apparatus of claim 1 wherein the readout is a sign.

7. The apparatus of claim 1 wherein the external magnetic field is the earth's magnetic field.

8. The apparatus of claim 1 wherein the external magnetic field is an applied electromagnetic field.

9. The apparatus of claim 1 wherein the housing is contained within a cylinder.

10. A self orienting floating apparatus comprising:
    a housing having a first end opposed to a second end,
    an orienting magnet attached to a pin, said pin having a first and second end,
    said orienting magnet attached to said first pin end,
    said second pin end affixed within said housing to said apparatus by a means to allow said orienting magnet to resistively rotate,
    and a means to rotate said orienting magnet to a predetermined position,
    such that when said orienting magnet is aligned with an external magnetic field, a
    readout of said apparatus orients itself in a direction pre-selected by a user, the pre-selected direction being independent of the external magnetic field.

11. The apparatus of claim 10 wherein the housing first end is smaller in diameter than the second end.

12. The apparatus of claim 10 wherein the housing first end is equal in diameter to the second end.

13. The apparatus of claim 10 wherein the orienting magnet is attached in a horizontal plane to a pinhead perpendicular to a pin axis, such that the poles of said orienting magnet are 180 degrees opposed to each other.

14. The apparatus of claim 10 wherein the means to allow the orienting magnet to resistively rotate comprises:
    a ferromagnetic nut having a central opening,
    a tube having a first open end opposed to a second end, and
    the pin having a pinhead on a first end, said pinhead larger in diameter than said central opening, said pinhead opposed to a pin second end, wherein
    the orienting magnet is affixed to said pinhead, said tube second end is in a fixed relation to the housing, said tube extending upward, said nut affixed to said tube first open end and aligned to allow passage of said pin second end until said pinhead rests on said nut, so that a space remains between said orienting magnet and said nut.

15. The apparatus of claim 14 wherein the tube second end is affixed to a ballast.

16. The apparatus of claim 14 wherein the tube second end is affixed to a first end of a thermometer barrel, said thermometer barrel terminating in a thermometer bulb.

17. The apparatus of claim 10 wherein the means to rotate said orienting magnet comprises a handheld direction setting magnet wherein the magnetic force between said orienting magnet and said handheld direction setting magnet is greater than the magnetic force between said orienting magnet and a ferromagnetic nut, allowing said handheld direction setting magnet to resistively rotate said orienting magnet.

18. A method for orienting a floating apparatus comprising the steps of:
    a) integrating an orienting magnet to said floating apparatus, such that a pin having a first and second end is affixed to said apparatus at said second pin end, said orienting magnet being attached to said first pin end, and
    b) orienting said orienting magnet relative to an external magnetic field such that when said orienting magnet aligns with said external magnetic field, a readout integral to said floating apparatus orients itself in a direction pre-selected by a user, the pre-selected direction being independent of the external magnetic field.

19. The method of claim 18 wherein the step of integrating the orienting magnet is resistively rotatably attaching said orienting magnet to the floating apparatus.

20. A self orienting floating apparatus comprising:

an orienting magnet attached to a pin, said pin having a first and second end, said orienting magnet attached to said first end, affixing said pin second end to said apparatus so that said orienting magnet will not rotate, such that when said orienting magnet is aligned with an external magnetic field, a readout of said apparatus orients itself in a direction pre-selected by a user, the pre-selected direction being independent of the external magnetic field.

21. The apparatus of claim 20 wherein the apparatus is a floating buoy.

22. The apparatus of claim 21 wherein the readout is a sign.

23. The method of claim 18 wherein the step of integrating the orienting magnet to said floating apparatus is such that a magnetic force between said orienting magnet and a handheld direction setting magnet is greater than a magnetic force between said orienting magnet and a ferromagnetic nut positioned to magnetically interact with said orienting magnet, thereby allowing said handheld direction setting magnet to resistively rotate said orienting magnet.

24. The method of claim 18 wherein the step of integrating the orienting magnet to said floating apparatus includes locating the orienting magnet external to the floating apparatus.

* * * * *